(12) United States Patent
Watkins et al.

(10) Patent No.: US 6,175,757 B1
(45) Date of Patent: *Jan. 16, 2001

(54) LUMINAL MAPPING

(75) Inventors: Ronald Dean Watkins, Niskayuna; Charles Lucian Dumoulin, Ballston Lake; Robert David Darrow, Scotia; Christine Elise Dumoulin, Ballston Lake, all of NY (US)

(73) Assignee: General Electric Company, Schenectady, NY (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/017,573

(22) Filed: Feb. 2, 1998

(51) Int. Cl.[7] .................................................. A61B 8/12
(52) U.S. Cl. ....................... 600/425; 600/462; 600/423; 128/916; 604/100
(58) Field of Search .............................. 128/916; 600/407, 600/424, 459, 462, 463, 467, 425, 423; 604/96, 99, 100, 103

(56) References Cited

U.S. PATENT DOCUMENTS

| | | | |
|---|---|---|---|
| 5,307,808 | | 5/1994 | Dumoulin et al. . |
| 5,377,678 | | 1/1995 | Dumoulin et al. . |
| 5,558,091 | * | 9/1996 | Acker et al. ....................... 128/653.1 |
| 5,588,432 | * | 12/1996 | Crowley ............................ 128/660.03 |
| 5,651,366 | * | 7/1997 | Liang et al. ...................... 128/662.06 |
| 5,704,361 | * | 1/1998 | Seward et al. ................... 128/662.06 |
| 5,724,978 | * | 3/1998 | Tenhoff ............................ 128/662.06 |
| 5,771,895 | * | 7/1998 | Slager .............................. 128/662.06 |
| 5,830,145 | * | 11/1998 | Tenhoff ................................. 600/463 |
| 5,924,990 | * | 7/1999 | Nachtomy et al. ................... 600/443 |

* cited by examiner

*Primary Examiner*—Marvin M. Lateef
*Assistant Examiner*—Eleni Mantis Mercader
(74) *Attorney, Agent, or Firm*—Jean K. Testa; Donald S. Ingraham

(57) ABSTRACT

An invasive probe for mapping the walls of a lumen employs a real-time tracking means and a wall distance measurement means. As the probe is advanced within the lumen, the real-time tracking means provides three-dimensional coordinates of the probe's position and orientation. Concurrent with probe localization, the distance between the probe and the lumen walls is measured. Both the probe position and the wall distance measurement are sent to a data acquisition system which in turn provides a graphic or numeric display to the operator. Probe tracking can be performed with radio-frequency, magnetic resonance, ultrasonic techniques or the like. If desired, lumen wall distance measurements can be performed with magnetic resonance or ultrasound methods. Lumen wall distance measurements can also be performed with mechanical devices such as balloons and/or expanding structures.

12 Claims, 7 Drawing Sheets

LUMINAL MAPPING

BACKGROUND OF THE INVENTION

1. Field of the Invention

This invention relates to medical imaging systems such as magnetic resonance, X-ray and ultrasound scanners, and more particularly to imaging systems designed to provide images of lumens within the body.

2. Discussion of Prior Art

Several methods are currently available for the in-vivo imaging of vessels and other lumens within the body. These include X-ray angiography, MR angiography and ultrasonic imaging. When X-ray procedures are employed to image lumens within the body, an X-ray opaque substance must be introduced into the lumen. For X-ray angiography, an iodinated contrast agent is typically injected into the bloodstream. For imaging the colon, on the other hand, a solution containing a Barium salt is frequently introduced into the patient. These contrast agents permit the visualization of the shape of the lumen by providing visual contrast between the inside of the lumen (which absorbs the X-rays) and the surrounding tissue (which is transparent to X-rays). Undesirable aspects of X-ray methods include the use of ionizing radiation, the use of toxic contrast agents and the difficulty of acquiring three-dimensional information without using a Computed Axial Tomography (CAT) scanner.

Magnetic resonance (MR) can also be used to make images of lumens within the body. Image contrast can be based upon velocity-induced phase shifts (as in phase-contrast MR angiography) or upon differences in $T_1$ caused by the injection of a $T_1$ relaxation agent. While MR imaging has the potential to discriminate between different types of lesions in a lumen wall and in many situations can be used to make diagnostic quality angiograms, the inherent low signal-to-noise ratio of MR imaging limits its spatial resolution.

In some parts of the body, ultrasonic imaging can be used to determine the shape of a lumen with a greater resolution that that available with magnetic resonance. Ultrasonic imaging can be acquired from outside the body using a hand-held probe applied next to the skin, or from inside the body using an ultrasonic imaging catheter. In both forms of ultrasonic imaging, the probe position and orientation are manipulated by the operator to maximize image quality and utility. Unfortunately, the exact position and orientation of the probe is not easily incorporated into the ultrasound image, since images are typically obtained without reference to an external or anatomical landmark.

Operator dependency is particularly severe when a vascular ultrasound probe is used. In these procedures, the probe is not held by the operator. Instead, the probe is placed at the end of a catheter which is inserted into a blood vessel. The catheter is manipulated by the operator, but must be followed with an X-ray fluoroscope to insure proper placement and orientation. The ultrasonic images collected by the probe is typically a cross-section of the vessel, but since the orientation of the probe can only be known with the X-ray fluoroscopic image, the ultrasonic image by itself cannot be used to provide information regarding the larger features of the vessel.

One alternative to using an X-ray image to locate an ultrasound catheter is to monitor the insertion depth of the catheter. This approach permits the reconstruction of data along the length of the vessel. Since no information is obtained about the orientation of the catheter within the vessel, however, the vessel can not be properly reconstructed into an image which shows the vessel's curvature and morphology. Reconstruction of ultrasonic images into larger data sets in which insertion depth is exclusively used to provide spatial information will be inherently and irreversibly distorted, particularly in regions of vessel curvature.

Several methods exist to follow the location of an invasive device within the body. These methods include MR tracking as disclosed in "Tracking System and Pulse Sequences to Monitor the Position of a Device Using Magnetic Resonance", C. L. Dumoulin, S. P. Souza and R. D. Darrow (U.S. Pat. No. 5,307,808) and radio frequency tracking as disclosed in "Tracking System to Follow the Position and Orientation of a Device Using Radio-Frequency Fields", C. L. Dumoulin, J. F. Schenck, and P. B. Roemer (U.S. Pat. No. 5,377,678). While these methods provide an instantaneous measurement of device location, they are not able to provide information about the diameter of a lumen.

What is needed is a means for acquiring high resolution images of luminal features such as location and wall composition within the body.

BRIEF DESCRIPTION OF THE DRAWINGS

The features of the invention believed to be novel are set forth with particularity in the appended claims. The invention itself, however, both as to organization and method of operation, together with further objects and advantages thereof, may be best understood by reference to the following description taken in conjunction with the accompanying drawing in which:

SUMMARY OF THE INVENTION

A system for acquisition of 3D images of a lumen of a subject makes use of a distance determination means incorporated into an insertion end of an invasive device. The distance determination device may be an ultrasonic beam which rotates to sense distance to lumen surface radially around the catheter, a mechanical expanding spring, or an inflatable balloon.

At least one device locating means is embedded in the insertion end of the invasive device.

A tracking means, being either radio-frequency (RF), or magnetic resonance (MR) tracking equipment, determines the instantaneous 3D location of the device locating means.

A signal interpretation device is coupled to the distance determination means and converts signals from the distance determination means into a measurement of the diameter of the lumen at its current 3D location.

The diameters and associated 3D locations are stored in a storage device until the lumen is measured over a desired area.

A 3D map of the lumen is created by the signal interpretation device by displaying the 3D locations and their associated diameters on the display device.

An operator may interact with the system to select the surfaces displayed, the viewpoint, color coding, and other display parameters.

OBJECTS OF THE INVENTION

It is an object of the present invention to provide a 3D map of the dimensions of a lumen of a subject.

It is another object of the present invention to diagnose luminal dysfunction employing a 3D luminal map of a subject.

DETAILED DESCRIPTION OF THE INVENTION

Figure 1:
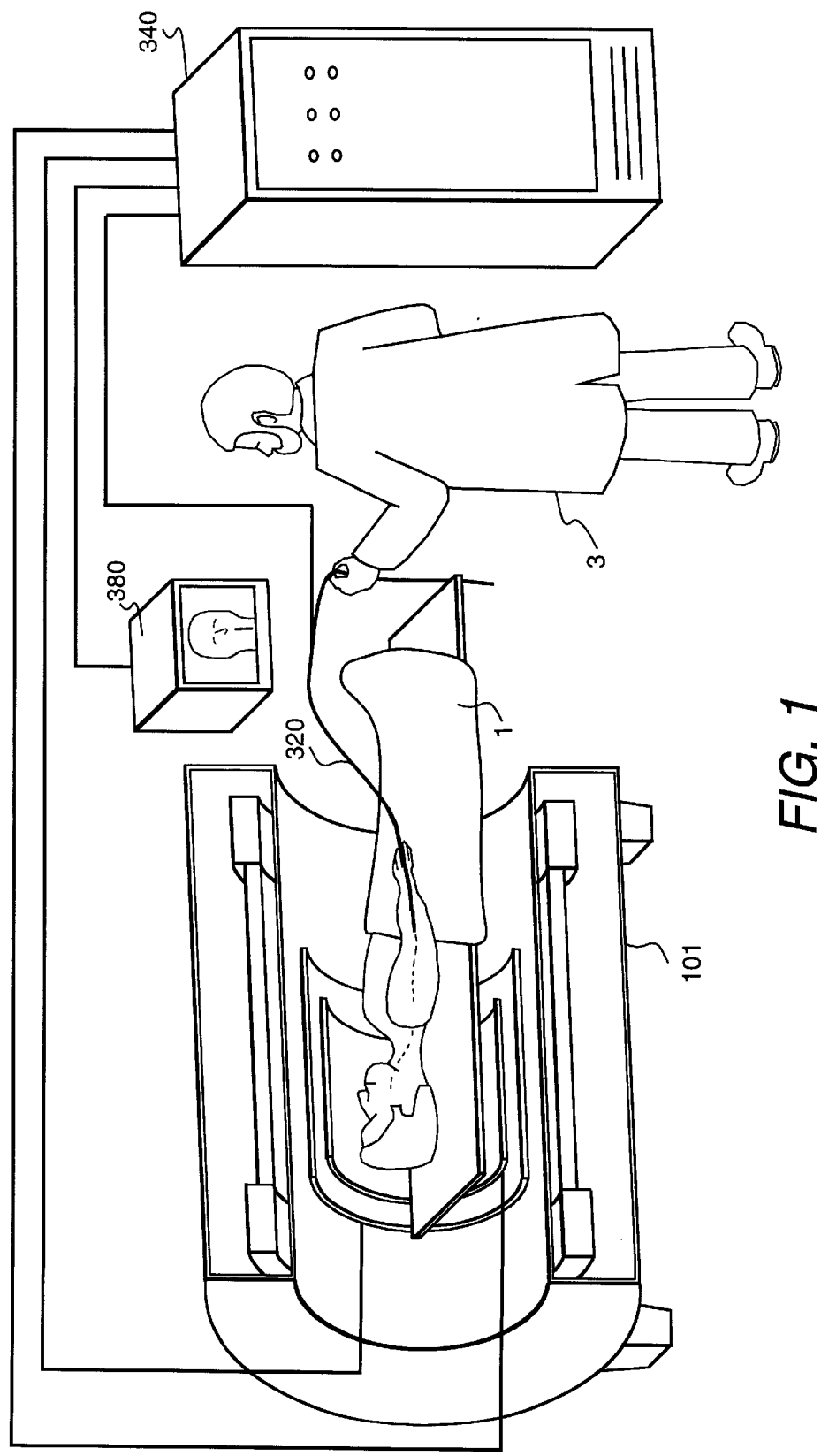
FIG. 1 is a simplified block diagram of an MR tracking system used to follow an invasive device in real-time (Prior Art).
Figure 2:
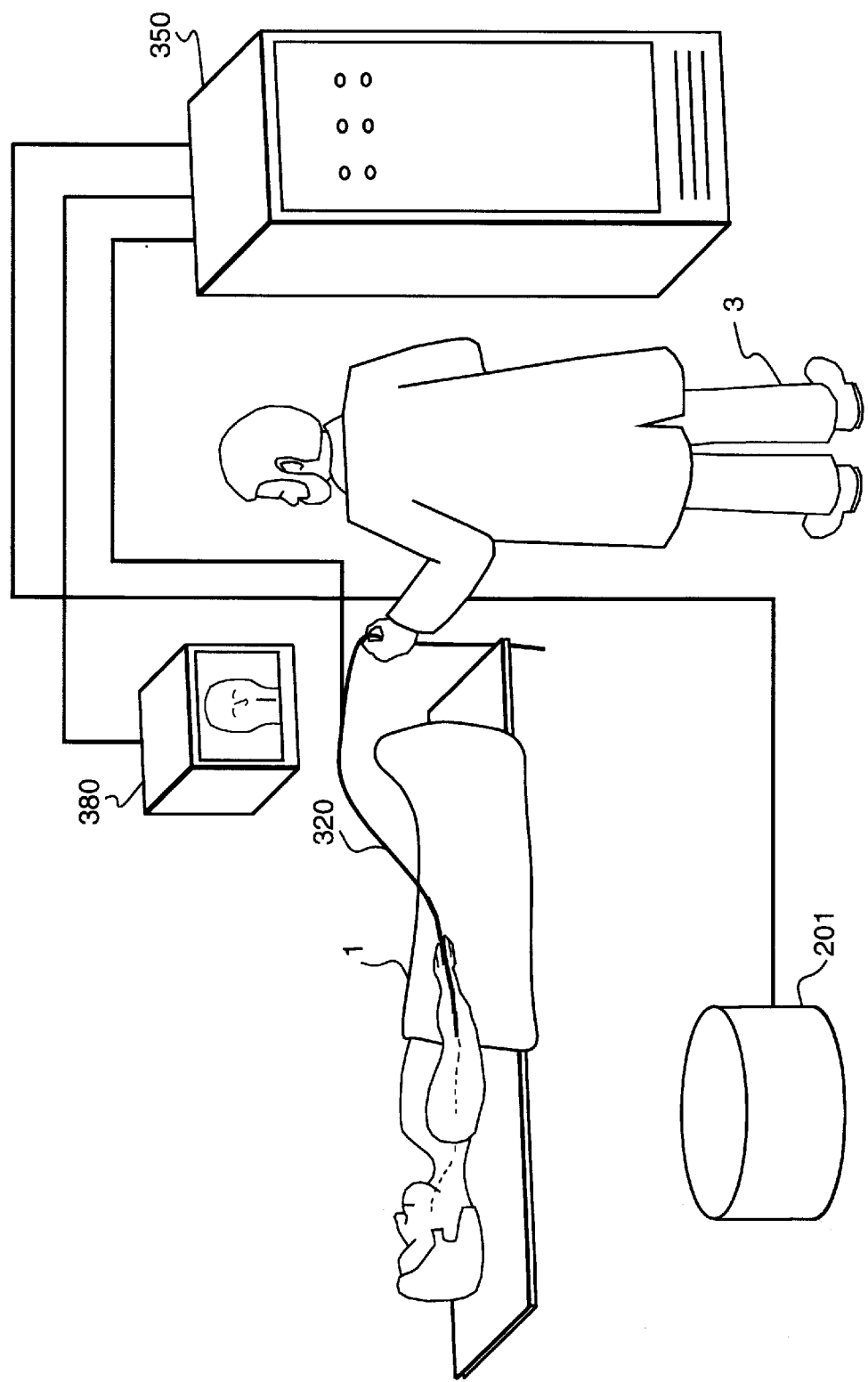
FIG. 2 is a simplified block diagram of an RF tracking system used to follow an invasive device in real-time (Prior Art).

Systems for creating a 3D map of cavities within a subject 1 according to the present invention are shown in FIGS. 1, and 2. These track the real-time location of an invasive device 320, such as a catheter within subject 1.

An operator 3, typically a Physician, inserts an invasive device 320 into a lumen of subject 1. Invasive device 320 has an element which is tracked by a tracking means. For magnetic resonance (MR) tracking, the tracked device maybe an MR coil, or a plurality of MR coils. These may be either receive or transmit coils. The tracked device may also be a quantity of a material which is imaged well in an MR image, such as copper sulfate solution.

The tracking means, as shown in FIG. 1, includes a magnet assembly 101 having RF and gradient coils, system electronics 340 and a display 380. The acquired MR signal is processed by the MR electronics 340 which interpret the signal into a location or plurality of locations which are tracked.

With RF tracking, as shown in FIG. 2, the tracked device may be an RF coil, or a plurality of RF coils attached to the invasive device 320. An external coil 201 operates to transmit an RF signal which is received by the RF coils attached to the invasive device 320. System electronics 350 interpret the signals to determine the location and orientation of invasive device 320 in real time. The location of invasive device 320 is displayed on a display 380.

In the alternative, external coil 201 may be a receive coil and the RF coils attached to invasive device 320 may be transmit coils.

Figure 3:
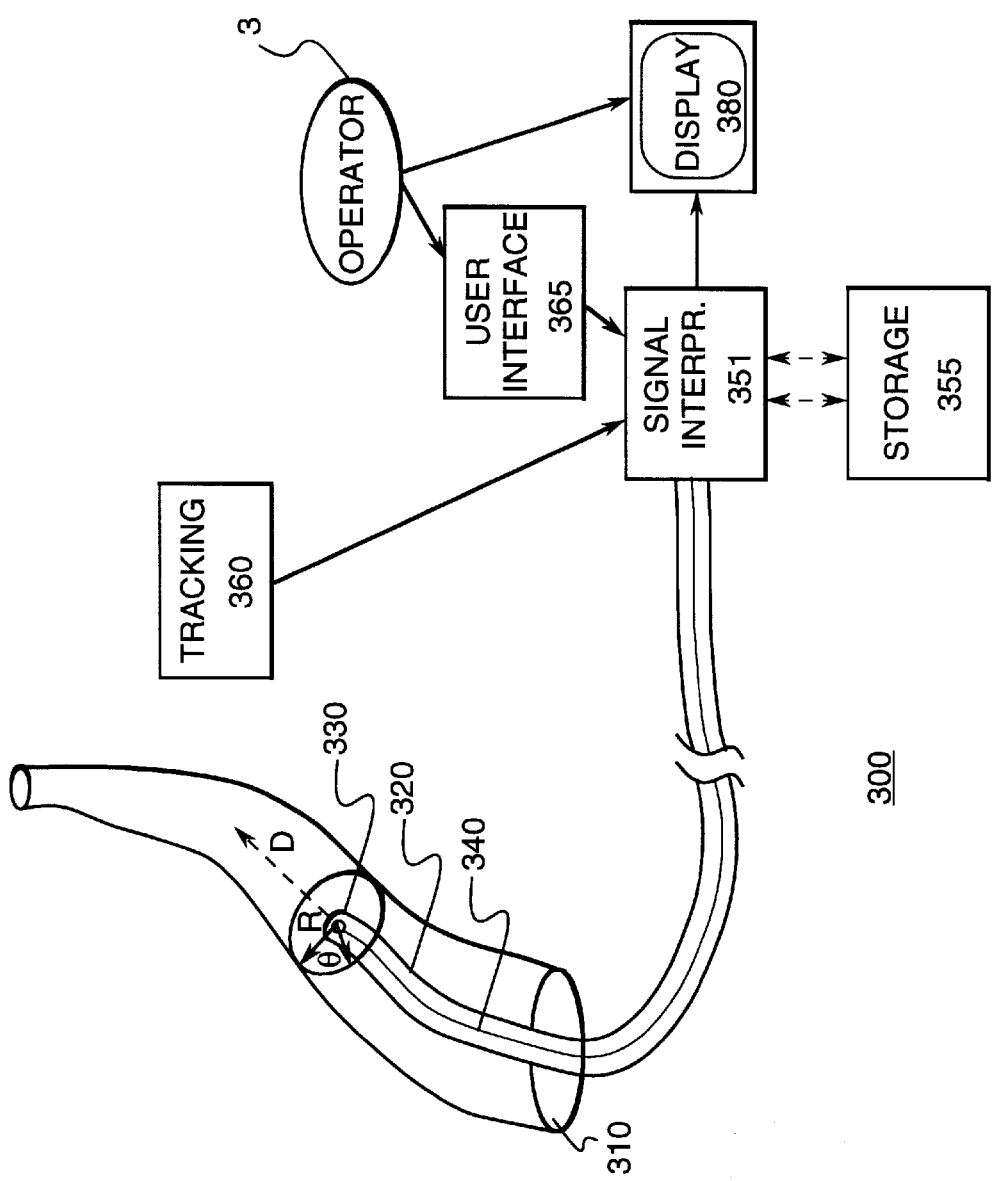
FIG. 3 is a simplified block diagram of a luminal mapping system according to the present invention for tracking a luminal probe in three dimensions, determining radial distances between the lumen wall and the probe, and creating a 3D image map.

In FIG. 3, a system 300 for the acquisition of a luminal image of a lumen 310 of subject 1 is shown. Lumen 310 may be a vessel, intestine, esophagus, stomach, or other cavity within the subject to be imaged. Lumen 310 may also include other body cavities, such as the abdominal cavity which are only accessible through an incision. Invasive device 320, incorporating a distance determination means 330, is inserted into lumen 310 and is used for determining a distance from the invasive device 320 to the inside wall of the lumen 310. The invasive device 320 is tracked by a device tracking means 360 which may be magnetic resonance (MR) tracking, or radio frequency (RF) tracking, ultrasonic tracking or other conventional tracking technology. The invasive device may be moved further in or retracted from luminal cavity 310 and therefore its displacement along the luminal cavity is measured as D.

A signal propagation means 340 connects the means for distance determination 330 to external equipment such as a signal interpretation device 351. Signal propagation means 340 may be, depending on the type of transducer used, an electric cable, or a fiber optic line.

Signal interpretation device 351 converts the signal from distance measurement means 330 into an actual distance measurement. The device tracking means 360 also provides the current location of invasive device 320 and therefore the location of distance determining means 330 to signal interpretation device 351.

As this information is collected it is stored in a storage device 355 for later reconstruction of a representation of the lumen wall. An operator may move invasive device inward or outward in order to attain information on different locations D within lumen 310. Distance measurement means 330 is designed to collect distance information shown as R for different angular displacements θ with reference to distance measurement device 330. Preferably, distance measurements R for different values of θ are made within a short time period of each other such that distance measurement device moves very little between measurements to provide accurate measurements.

Operator 3 may then interact with a user interface 365 attached to signal interpretation device 351 in order to request that signal interpretation device 351 display the stored representation of lumen 310 on a display device 380.

Figure 4:
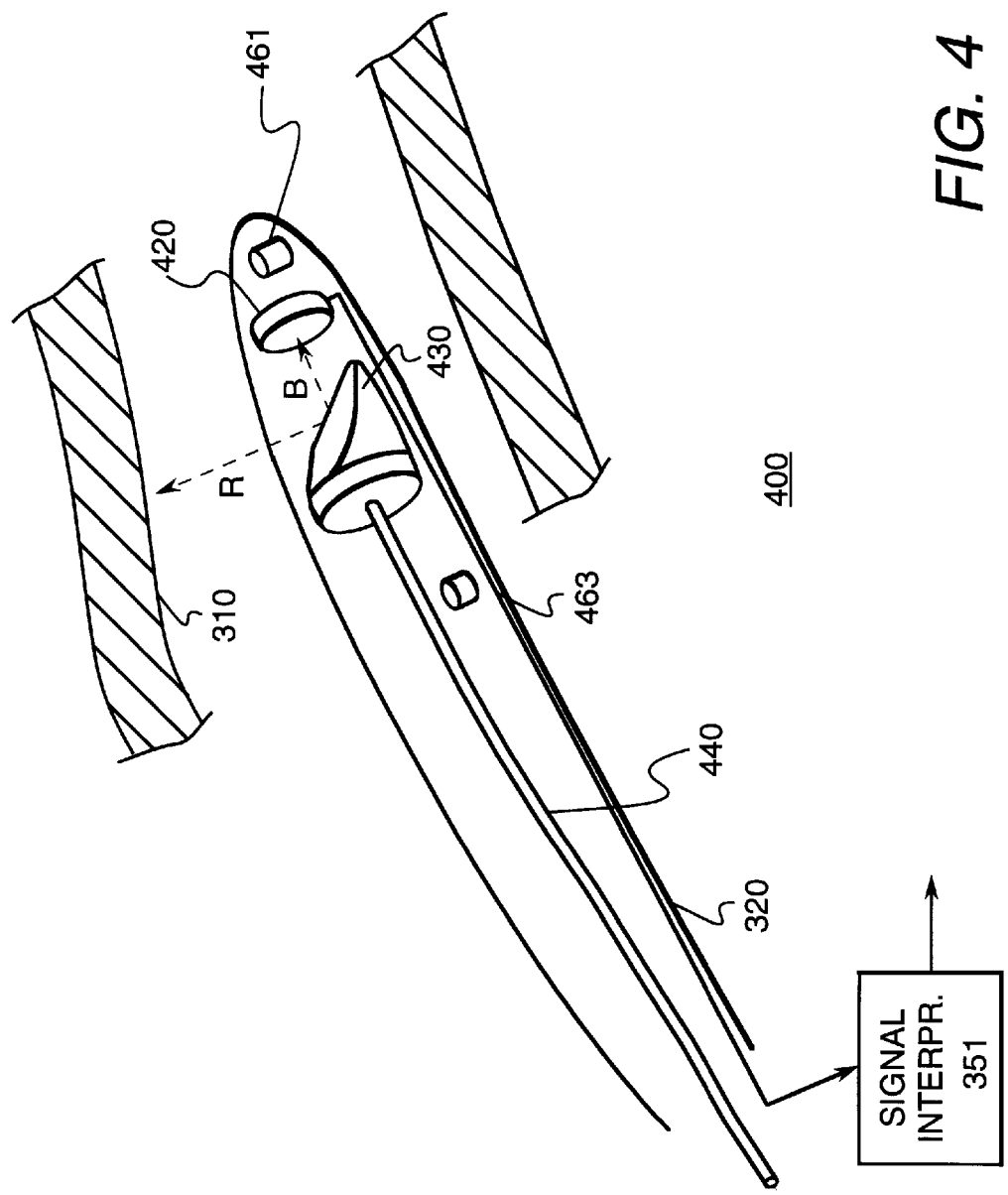
FIG. 4 is a simplified block diagram of a luminal mapping system according to the present invention in which ultrasound is used to determine the distance to the lumen wall.

FIG. 4 shows an ultrasonic embodiment 400 of invasive device 320 of FIG. 3 in a more detailed diagram. The embodiment of FIG. 4 employs a piezo-electric ultrasound transducer 420 to produce an ultrasound beam B. This ultrasound beam B reflects off of a planar acoustic mirror 430 angled such that the beam passes outside of the catheter and intersects the lumen wall 310. In this embodiment housing of invasive device 320 is comprised of an acousto-transparent material thereby allowing the ultrasonic beam to pass through it with little attenuation. In an alternative embodiment the acoustic material may be made in a circular window passing around the perimeter of the invasive device 320. The planar acoustic mirror 430 is attached to a flexible rotating shaft 440. The rotating shaft turns and consequently turns the planar acoustic mirror 430 causing the ultrasound beam to be reflected at different angular variations θ around the perimeter of invasive device 320.

Ultrasonic beam B reflected from lumen wall 310 again reflects off of acoustic mirror 430 and is received by piezo-electric ultrasound transducer 420.

The signal from transducer 420 is passed back through the invasive device to signal interpretation device 351 determining the instantaneous distance R at a plurality of angular variations θ around invasive device 320.

A first device locating means 461 and a second device locating means 463 are attached to invasive device 320 at known locations relative to planar acoustic mirror 430. These device locating means are related to the device tracking means 360 such that they are targets which are tracked by device tracking means 360. For example, these may be small RF coils which may tracked by an MR tracking device 360. In still another alternative embodiment, 461, 463 may be RF coils which are tracked by an RF tracking means. The MR tracking means and RF tracking means are known in the art.

Figure 5:
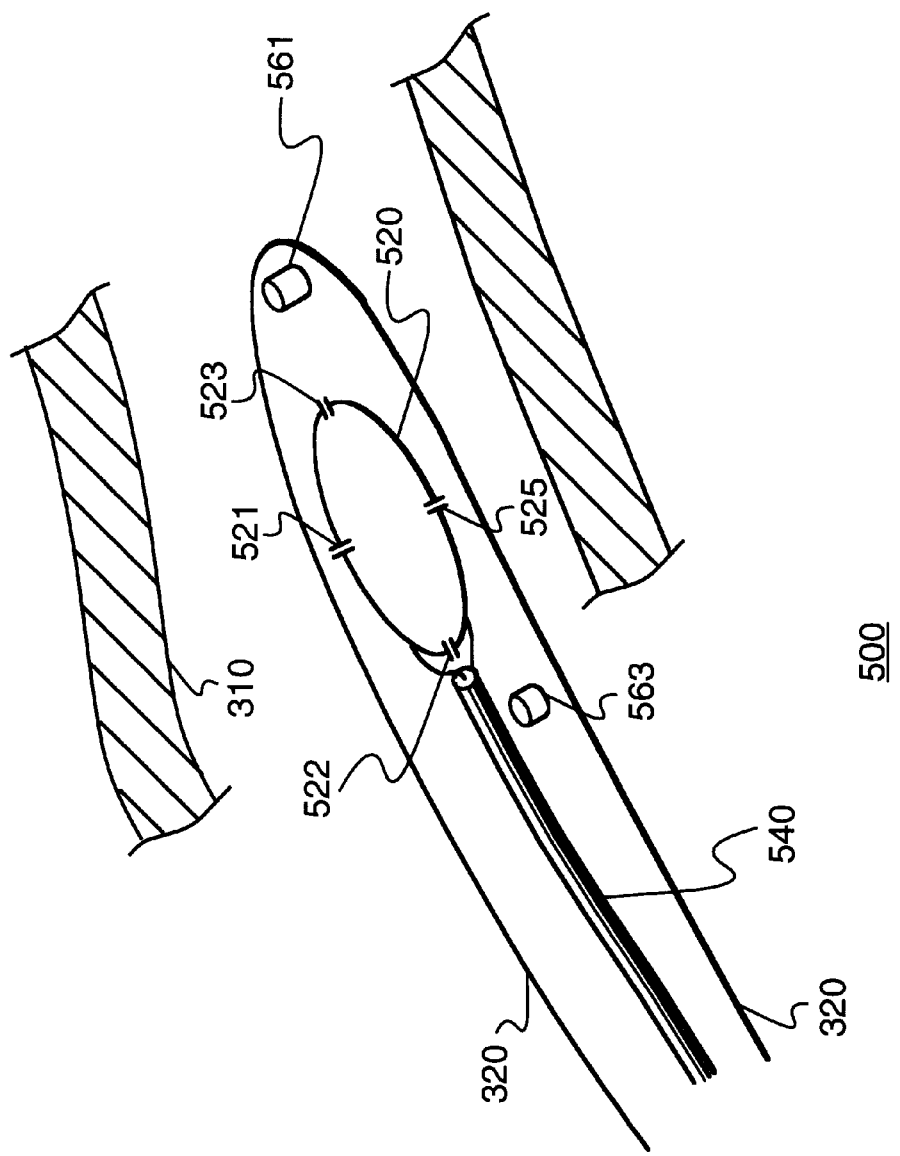
FIG. 5 is a simplified block diagram of a luminal mapping system according to the present invention in which an MR coil is used to determine the distance to the lumen wall.

In FIG. 5, an MR luminal probe 500 is shown. In this embodiment an MR receive coil 520 is shown connected to a coaxial cable 540 which propagates signals detected by the MR receive coil to outside equipment.

MR receive coil 520 may or may not be tuned to the Larmor frequency of tissue of subject 1 desired to be imaged. A tuned coil provides a more sensitive receptor to MR signals, however, and it may be desirable to incorporate tuning capacitors 521, 523 and 525. This may make MR receive coil 520 larger and more bulky.

If desired, a matching capacitor 522 can be used to match the receive coil. Again, a first device locating means 561 and a second device locating means 563 are used to track the location of the invasive device 320. Only one of the devices is required to determine location, however, two or more device also provide an orientation of the invasive device.

Receive coil 520 receives MR signals from lumen 310 and can provide a localized image of the lumen using MR imaging sequences. These images, combined with the information D of the depth within the lumen the invasive device may be used to provide a three-dimensional image of the inside of lumen 310.

Figure 6:
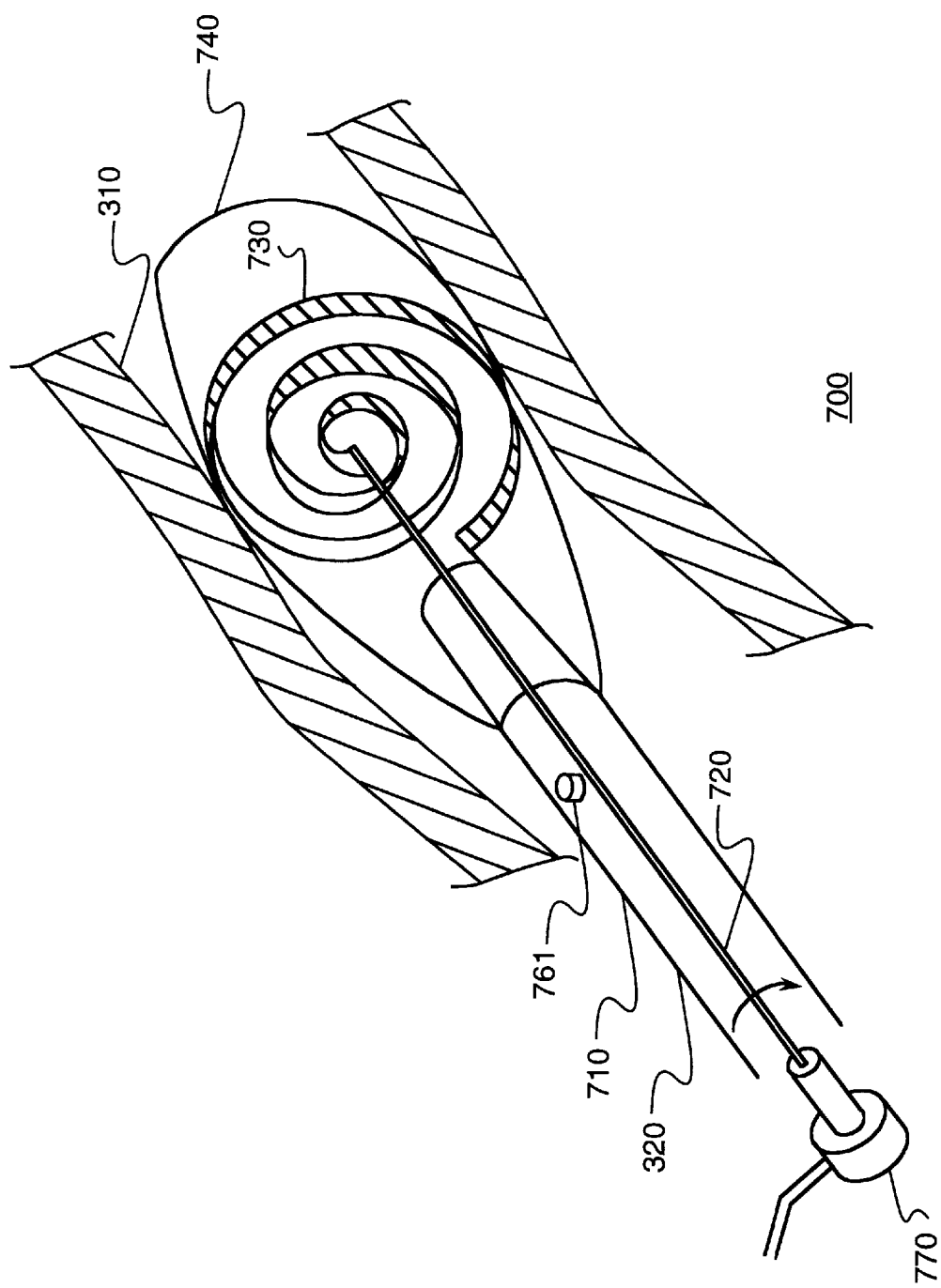
FIG. 6 is a simplified block diagram of a luminal mapping system according to the present invention in which a mechanical spiral coil is used to determine the distance to the lumen wall.

In FIG. 6, a mechanical luminal probe 700 is shown which measures lumen diameter. Invasive device 320 employs a rotating shaft 720 which runs the length of the invasive device and connects to a spiral spring 730. Spiral spring is rolled into a small diameter such that it may move freely through lumen 310. At a selected position within the lumen rotating shaft 720 is rotated to allow spiral spring 730 to expand until a difference in torsional force is sensed. Rotating shaft 720 may be rotated manually by an operator or it may be rotated by a motor 770 designed to sense a difference in torsional force. An elastic sock 740 such as a latex balloon may be used to cover spiral spring 730 and rotating shaft 720 to ease maneuvering through lumen 310.

Again, at least one device locating means 761 is employed to determine the location within the lumen of the luminal probe.

Figure 7:
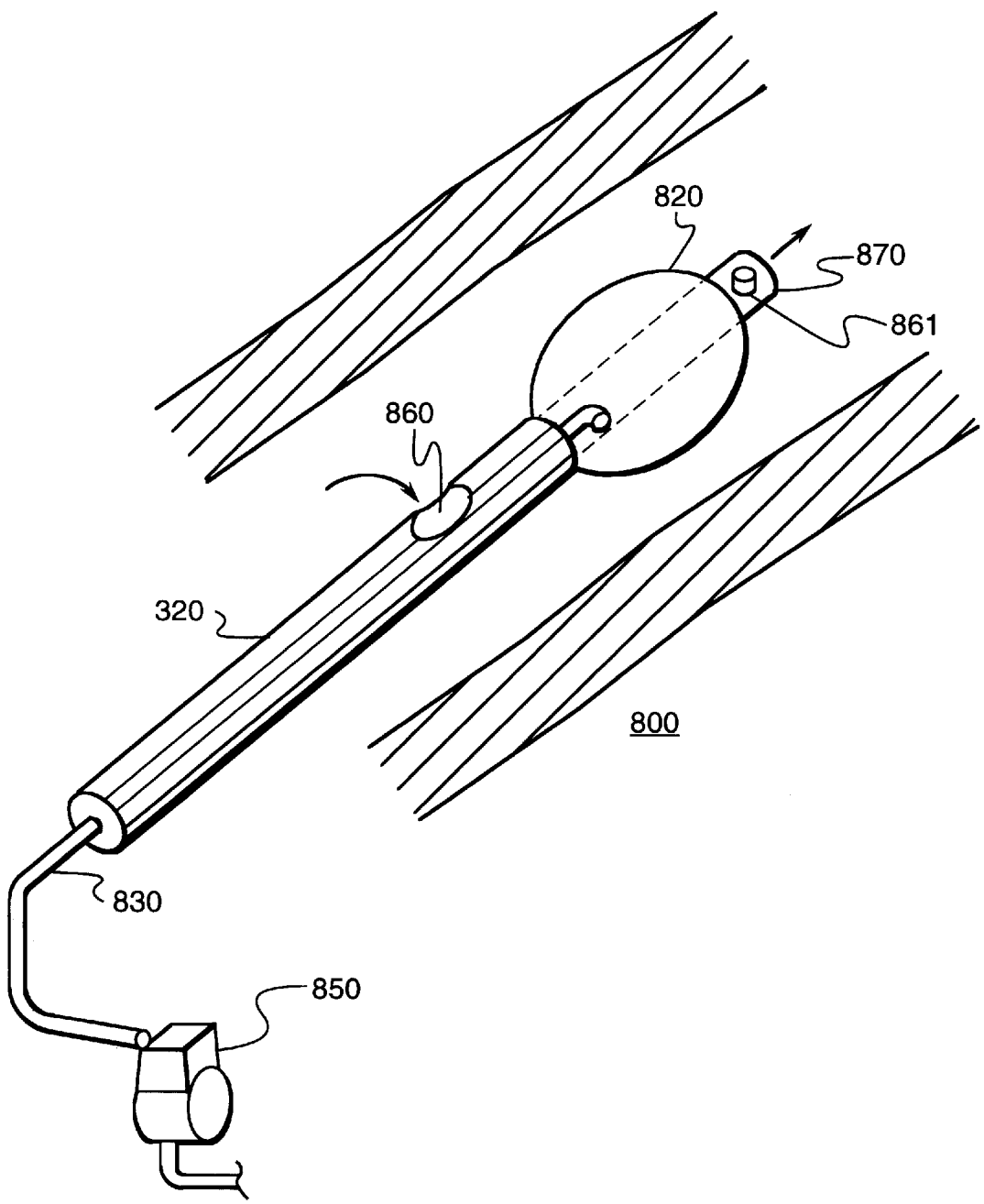
FIG. 7 is a simplified block diagram of a luminal mapping system according to the present invention in which an inflatable balloon is used to determine the distance to the lumen wall.

In FIG. 7, an inflatable luminal probe 800 is shown in which an inflatable balloon 820 expands when a metered amount of fluid is pumped into balloon 820 through pipe 830 which is connected to a metering pump 850. The fluid may be water, water solutions, air, or other gasses.

Metering pump 850 keeps track of the volume of fluid which is pumped into inflatable balloon 820. This information is passed then to signal interpretation device which has been pre-calibrated to determine a diameter based upon the volume of fluid pumped into balloon 820.

Since inflatable luminal mapping probe 800 completely blocks the lumen, there may be a need for a bypass such as when it is employed in vessels. In this case, an inlet 860 is employed which passes a biological fluid, such as blood, through the length of the probe housing and out through an outlet 870. This inlet and outlet bypass may be employed on any of the other luminal mapping probe embodiments above which substantially block the lumen and require a bypass of a fluid.

Again, a device locating means 861 is tracked by tracking means 360.

While several presently preferred embodiments of the novel invention have been described in detail herein, many modifications and variations will now become apparent to those skilled in the art. It is, therefore, to be understood that the appended claims are intended to cover all such modifications and variations as fall within the true spirit of the invention.

What we claim is:

1. A system creating a 3D image of a lumen of a subject comprising:
    a) an invasive device for insertion into a lumen of a subject;
    b) a distance determination means incorporated into an insertion end of the invasive device for measuring a distance from the insertion end to the inside wall of the lumen at a plurality of angular locations;
    c) at least one device locating means located in the invasive device;
    d) a tracking means for tracking the device locating means as an operator moves the invasive device in the subject to determine an instantaneous 3D location of the invasive device;
    e) a storage device for storing 3D locations and measured distances for later retrieval;
    f) a display device for providing graphical displays to the operator; and
    g) a signal interpretation device coupled to the distance determination means and storage device for retrieving the stored measured distances and stored 3D locations to create and display on the display device 3D images of lumen according to operator movement of the invasive device.

2. The system for creating a 3D image of a lumen of claim 1 wherein the tracking means comprises:
    magnetic resonance (MR) tracking equipment.

3. The system for creating a 3D image of a lumen of claim 1 wherein the tracking means comprises:
    radio-frequency (RF) tracking equipment.

4. The system for creating a 3D image of a lumen of claim 1 wherein the distance determination means comprises:
    ultrasonic distance measurement equipment.

5. The system creating a 3D image of a lumen of claim 4 wherein the ultrasonic distance measurement equipment comprises:
    a) an ultrasonic beam transducer for providing an ultrasonic beam along an axis, and for sensing incident ultrasonic energy;
    b) a rotatable ultrasonic mirror angled with respect to an axis of ultrasonic beam for reflecting the ultrasonic beam to a plurality of radial locations of the lumen around the axis of the ultrasonic beam, the ultrasonic transducer receiving ultrasonic energy reflected back from the lumen and providing the ultrasonic energy to the signal interpretation device.

6. The system for creating a 3D image of a lumen of claim 1 wherein the distance determination means comprises at least one magnetic resonance (MR) receive coil for receiving an MR signal from surrounding lumen, and for passing the received MR signal to the signal interpretation device.

7. The system for creating a 3D image of a lumen of claim 1 wherein the distance determination means comprises a mechanical expansion device.

8. The system for creating a 3D image of a lumen of claim 7 wherein the mechanical expansion device comprises:
    a) a shaft free to rotate through an angle θ with respect to invasive device;
    b) a spiral spring having a center end and an outer end, the center end connected to the shaft with the outer end fixed with respect to the invasive device;

c) a rotation means connected to the shaft capable of rotating the shaft and for equating rotation $\theta$ to diameter of spiral spring, and for passing the diameter to signal interpretation device.

9. The system for creating a 3D image of a lumen of claim 8 further comprising:

an elastic sock attached to invasive device surrounding spiral spring facilitating movement of invasive device through lumen.

10. The system for creating a 3D image of a lumen of claim 1 wherein the distance determination means comprises an inflatable expansion device.

11. The system for creating a 3D image of a lumen of claim 10 wherein the inflatable expansion device comprises:

a) an inflatable balloon;
b) an inflater pipe coupled to the inflatable balloon;
c) a calibrated metering pump operating to pump fluid into, or out of, inflatable balloon though inflater pipe, operating to keep track of the amount of fluid in inflatable balloon, and for calculating lumen diameter based upon the amount of fluid in inflatable balloon.

12. The system for creating a 3D image of a lumen of claim 1 further comprising:

a user interface coupled to the signal interpretation device for acquiring operator defined input and for providing this input to the signal interpretation device.

* * * * *